US012694970B2

(12) United States Patent
Akagi et al.

(10) Patent No.: US 12,694,970 B2
(45) Date of Patent: Jul. 28, 2026

(54) DISPLAY APPARATUS, IMAGE MANAGEMENT SERVER, AND RECORDING MEDIUM

(71) Applicant: Konica Minolta, Inc., Tokyo (JP)

(72) Inventors: Eiichi Akagi, Hachioji (JP); Yozo Okubo, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 610 days.

(21) Appl. No.: 18/158,780

(22) Filed: Jan. 24, 2023

(65) Prior Publication Data

US 2023/0245760 A1 Aug. 3, 2023

(30) Foreign Application Priority Data

Jan. 28, 2022 (JP) ................................ 2022-011407

(51) Int. Cl.
| | |
|---|---|
| *G16H 30/20* | (2018.01) |
| *G06F 3/14* | (2006.01) |
| *G06T 7/20* | (2017.01) |
| *G16H 15/00* | (2018.01) |

(52) U.S. Cl.
CPC .............. *G16H 30/20* (2018.01); *G06F 3/14* (2013.01); *G06T 7/20* (2013.01); *G16H 15/00* (2018.01); *G06T 2207/10116* (2013.01)

(58) Field of Classification Search
CPC .......... G16H 30/20; G06H 15/00; G06F 3/14; G06T 7/20; G06T 2207/10116
USPC ....................................................... 382/132
See application file for complete search history.

(56) References Cited

U.S. PATENT DOCUMENTS

| | | | | |
|---|---|---|---|---|
| 2009/0248447 A1* | 10/2009 | Niwa | ..................... | G16H 15/00 |
| | | | | 707/E17.014 |
| 2012/0131498 A1* | 5/2012 | Gross | .................. | G06F 3/04842 |
| | | | | 715/788 |
| 2013/0131465 A1* | 5/2013 | Yamamoto | ........... | A61B 5/7271 |
| | | | | 600/300 |
| 2015/0032471 A1* | 1/2015 | Arazi | ..................... | G16H 15/00 |
| | | | | 705/3 |
| 2021/0369225 A1* | 12/2021 | Nanjo | .................... | A61B 6/486 |
| 2023/0238118 A1* | 7/2023 | Nakamura | ............. | G16H 15/00 |
| | | | | 705/2 |

FOREIGN PATENT DOCUMENTS

| | | |
|---|---|---|
| JP | 2006260301 A | 9/2006 |
| JP | 2008198135 A | 8/2008 |
| JP | 2013081579 A | 5/2013 |
| JP | 2021177792 A | 11/2021 |

OTHER PUBLICATIONS

JPO Notice of Reasons for Refusal for corresponding JP Application No. 2022-011407; issued Aug. 5, 2025.
JPO Decision of Refusal for corresponding JP Application No. 2022-011407; Issued Nov. 11, 2025.

* cited by examiner

*Primary Examiner* — Gabriel I Garcia
(74) *Attorney, Agent, or Firm* — CANTOR COLBURN LLP

(57) ABSTRACT

Provided is a display apparatus including a hardware processor that acquires, from an external apparatus, a radiology report to which a dynamic image acquired by irradiating and dynamically radiographing a subject with radiation or a dynamic analysis image indicating a result of analyzing the dynamic image is attached; and a display that displays the acquired radiology report.

11 Claims, 5 Drawing Sheets

DISPLAY APPARATUS, IMAGE MANAGEMENT SERVER, AND RECORDING MEDIUM

CROSS REFERENCES TO RELATED APPLICATIONS

The present invention claims priority under 35 U.S.C. § 119 to Japanese Application, 2022-011407, filed on Jan. 28, 2022, the entire contents of which being incorporated herein by reference.

TECHNICAL FIELD

The present invention relates to a display apparatus, an image management server, and a recording medium.

DESCRIPTION OF THE RELATED ART

In the related art, an image management server is known to be installed in a medical facility to manage medical images radiographed at the medical facility (for example, see JP 2006-260301A).

Recently, images are being shared with an external medical facility through an external image management server (for example, a cloud-based image server).

For example, when a clinic wants to conduct an examination of a patient, but the clinic lacks a radiographic apparatus necessary for the examination, the clinic may request an examination at another medical facility such as a large hospital and make a diagnosis at the clinic using obtained images. In such cases, a recording medium such as DVD-R is often used to transfer images, but since the recording medium is handed to the patient, there are problems in that preparing the recording medium takes time and labor, and there is a risk that the recording medium may be lost. Accordingly, in recent years, a method of transferring images online through an external image management server such as a cloud-based image server is also being used.

SUMMARY OF THE INVENTION

Incidentally, dynamic radiography has recently been introduced to radiography. With dynamic radiography, a dynamic image containing hundreds of frame images may be acquired from a single radiographic capture, resulting in a large amount of data. The same is true of a dynamic analysis image indicating the result of analyzing a dynamic image. For this reason, if a dynamic image or a dynamic analysis image is downloaded directly to a low-performance display apparatus, there are problems in that the download may be time-consuming and the display apparatus may freeze due to being unable to handle the large amount of data. Moreover, there are also problems such as the data occupying much of the storage capacity.

An object of the present invention is to enable the efficient display, on a display apparatus, of a dynamic image and a dynamic analysis image stored in an external apparatus such as an image management server.

To achieve at least one of the abovementioned objects, according to an aspect of the present invention, a display apparatus reflecting one aspect of the present invention comprises:

a hardware processor that acquires, from an external apparatus, a radiology report to which a dynamic image acquired by irradiating and dynamically radiographing a subject with radiation or a dynamic analysis image indicating a result of analyzing the dynamic image is attached; and a display that displays the acquired radiology report.

To achieve at least one of the abovementioned objects, according to an aspect of the present invention, an image management server reflecting one aspect of the present invention comprises:

storage that stores a radiology report to which a dynamic image acquired by irradiating and dynamically radiographing a subject with radiation or a dynamic analysis image indicating a result of analyzing the dynamic image is attached; and a hardware processor that acquires the radiology report from the storage and generates a display image for displaying the acquired radiology report on an external display apparatus.

To achieve at least one of the abovementioned objects, according to another aspect of the present invention, a storage medium reflecting one aspect of the present invention is a non-transitory recording medium storing a computer readable program causing a computer of a display apparatus that includes a display to function as:

an acquirer that acquires, from an external apparatus, a radiology report to which a dynamic image acquired by irradiating and dynamically radiographing a subject with radiation or a dynamic analysis image indicating a result of analyzing the dynamic image is attached; and a display controller that causes the display to display the radiology report acquired by the acquirer.

To achieve at least one of the abovementioned objects, according to another aspect of the present invention, a storage medium reflecting one aspect of the present invention is a non-transitory recording medium storing a computer readable program causing a computer to function as:

an acquirer that acquires a radiology report from storage that stores the radiology report, a dynamic image acquired by irradiating and dynamically radiographing a subject with radiation or a dynamic analysis image indicating a result of analyzing the dynamic image being attached to the radiology report; and an image generator that generates a display image for displaying the radiology report acquired by the acquirer on an external display apparatus.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION

Hereinafter, one or more embodiments of the present invention will be described with reference to the drawings. However, the scope of the invention is not limited to the disclosed embodiments or illustrated examples.

First Embodiment

[Configuration of Image Management System 100]

Figure 1:
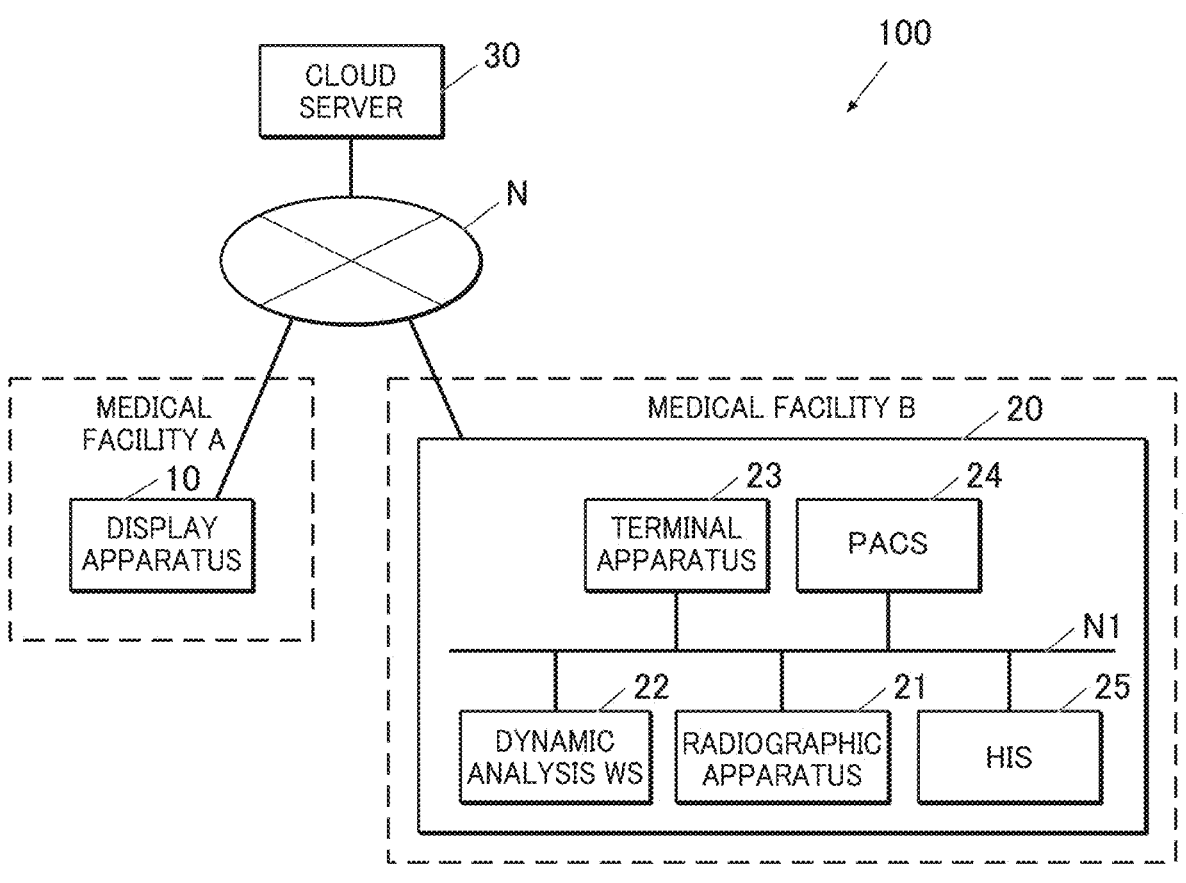
FIG. 1 is a diagram illustrating an overall configuration example of an image management system according to the present embodiment.

FIG. 1 is a diagram illustrating a system configuration example of an image management system 100 according to an embodiment of the present invention.

As illustrated in FIG. 1, the image management system 100 includes a display apparatus 10 installed in a medical facility A, an in-house system 20 installed in a medical facility B, and a cloud server 30, the above being communicably connected through a communication network N to allow for the transmission and reception of data.

The medical facility A is a facility, such as a clinic, for example, that lacks a radiographic apparatus that performs dynamic radiography inside the facility. The medical facility B is a facility, such as a core hospital, for example, which includes a radiographic apparatus 21 capable of dynamic radiography and which conducts an examination by dynamic radiography based on an examination request from the medical facility A. The cloud server 30 is an image management server that provides medical collaboration services, such as the handover of image data between the medical facility A and the medical facility B.

Note that the number of medical facilities A on the examination-requesting side and the number of medical facilities B on the examination-conducting side are not particularly limited.

Here, dynamic radiography refers to the acquisition of a plurality of images indicating a dynamic state of a subject by repeated irradiation of the subject with pulses of radiation such as X-rays at predetermined time intervals according to a single radiographic operation (pulse irradiation), or by continuous, uninterrupted irradiation of the subject at a low dose rate (continuous irradiation). The series of images obtained by dynamic radiography is referred to as a dynamic image. Also, each of the plurality of images forming the dynamic image is referred to as a frame image. Also, an image indicating a result of analyzing a dynamic image is referred to as a dynamic analysis image.

Dynamic radiography encompasses moving image capture but does not encompass the capturing of a still image while displaying a moving image. A dynamic image encompasses a moving image but does not encompass an image obtained by capturing a still image while displaying a moving image.

[Configuration of Display Apparatus 10]

The display apparatus 10 is an apparatus for archiving and displaying medical images that a physician uses to make a diagnosis in the medical facility A. The display apparatus 10 includes an integrated apparatus combining a picture archiving and communication system (PACS), a viewer which is a medical image display apparatus running in the cloud, a console of a medical imaging apparatus, and a medical image management apparatus.

Figure 2:
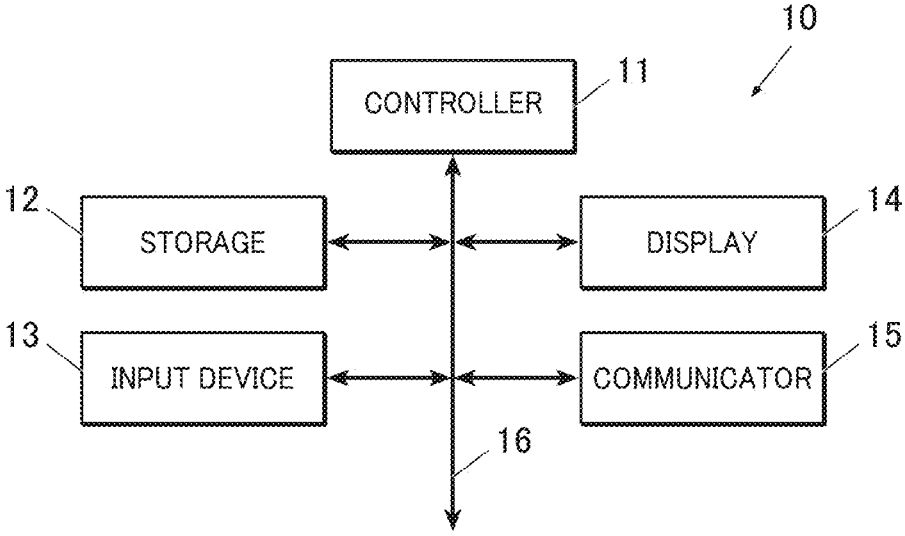
FIG. 2 is a block diagram illustrating a functional configuration of a display apparatus in FIG. 1.

FIG. 2 is a block diagram illustrating a functional configuration of the display apparatus 10. As illustrated in FIG. 2, the display apparatus 10 is provided with a controller 11 (hardware processor), storage 12, an input device 13, a display 14, a communicator 15, and the like, the above being connected by a bus 16.

The controller 11 includes a central processing unit (CPU), a random access memory (RAM), and/or the like. The CPU of the controller 11, in response to an operation performed on the input device 13, reads out a system program and any of various processing programs stored in the storage 12, loads the programs into the RAM, and centrally controls operations by each component of the display apparatus 10 according to the loaded programs. The controller 11 also executes the processing on the display apparatus 10 side illustrated in FIG. 4 according to a medical collaboration program stored in the storage 12. The controller 11 cooperates with the communicator 15 to function as an acquirer of the display apparatus of the present invention. The controller 11 also cooperates with the input device 13 to function as a selector of the display apparatus of the present invention.

The storage 12 includes a non-volatile semiconductor memory, a hard disk, and/or the like. The storage 12 stores various programs to be executed by the controller 11, parameters necessary for the execution of processing by the programs, and/or data such as processing results. For example, the storage 12 stores the medical collaboration program described above. The medical collaboration program is a program for receiving a medical collaboration service provided by the cloud server 30. The various programs are stored in the form of readable program code, and the controller 11 sequentially executes operations in accordance with the program code.

Additionally, the storage 12 stores medical images radiographed inside the medical facility A and medical images (in the present embodiment, dynamic images or dynamic analysis images (or both)) and radiology reports downloaded from the cloud server 30 in association with patient information (such as a patient ID and the patient's name, date of birth, and age, for example) about the examinee and examination information (such as an examination date, an examination area, the type of dynamic analysis, and a request ID described later, for example).

The input device 13 is provided with a keyboard furnished with cursor keys, numerical input keys, any of various types of function keys, and the like, and a pointing device such as a mouse, and outputs to the controller 11 an instruction signal inputted by a key operation on the keyboard and/or a mouse operation performed by a user. The input device 13 may also be provided with a touch panel on the display screen of the display 14, and in this case the input device 13 outputs to the controller 11 an instruction signal inputted through the touch panel.

The display 14 includes a monitor such as a liquid crystal display (LCD) panel or a cathode-ray tube (CRT) monitor and displays an input instruction from the input device 13, data, and/or the like according to the instruction of a display signal inputted from the controller 11.

The communicator 15 transmits and receives various data to and from external equipment connected to the communication network N.

[Configuration of in-House System 20]

The in-house system 20 is a system set up inside the medical facility B, in which a radiographic apparatus 21, a dynamic analysis workstation (WS) 22, a terminal apparatus 23, a PACS 24, and a hospital information system (HIS) 25 are connected through a communication network N1 such as a local area network (LAN).

The radiographic apparatus 21 is a medical imaging apparatus that can acquire a dynamic image containing a plurality of frame images indicating a dynamic state of a subject by irradiating the subject with radiation to perform dynamic radiography.

The dynamic analysis WS 22 is a workstation that analyzes the motion of the subject in the dynamic image acquired by the radiographic apparatus 21 and generates a dynamic analysis image indicating an analysis result.

The analysis performed by the dynamic analysis WS 22 may be, for example, ventilatory analysis and/or blood flow analysis performed on a dynamic image of the chest. The dynamic analysis WS 22 generates a ventilatory analysis image by performing ventilatory analysis on a dynamic image of the chest. Also, the dynamic analysis WS 22 generates a blood flow analysis image by performing blood flow analysis on a dynamic image of the chest.

For example, through ventilatory analysis, the dynamic analysis WS 22 calculates an index value indicating the ventilatory volume for each pixel (or for each small region containing multiple pixels) of each frame image in a dynamic image of the chest.

For example, through ventilatory analysis, the dynamic analysis WS 22 calculates, as the index value indicating the ventilatory volume for each pixel of each frame image, a difference value (the absolute value of the difference; the value may also be a ratio) between the signal value of each pixel of each frame image in a dynamic image and the signal value of a corresponding pixel (for example, the pixel at the same coordinate position) of an analysis reference frame image serving as a reference in analysis. Additionally, a color is added to each pixel of each frame image according to the calculated index value indicating the ventilatory volume. The analysis reference frame image can be obtained by, for example, calculating the change over time in the signal value for each of pixels that correspond to each other between frame images, and treating the frame image with the lowest signal value (that is, the frame image when the region is maximally contracted) as the analysis reference frame image for that pixel.

As another example, through blood flow analysis, the dynamic analysis WS 22 calculates an index value indicating the blood flow volume for each pixel (or for each small region containing multiple pixels) of each frame image in a dynamic image of the chest.

For example, through blood flow analysis, the dynamic analysis WS 22 calculates, as the index value indicating the blood flow volume for each pixel of each frame image, a difference value (the absolute value of the difference; the value may also be a ratio) between the signal value of each pixel of each frame image in a dynamic image and the signal value of a corresponding pixel (for example, the pixel at the same coordinate position) of an analysis reference frame image serving as a reference in analysis. Additionally, a color is added to each pixel of each frame image according to the calculated index value indicating the blood flow volume. The analysis reference frame image can be obtained by, for example, calculating the change over time in the signal value for each of pixels that correspond to each other between frame images, and treating the frame image with the highest signal value (that is, the frame image when the blood flow is the least) as the analysis reference frame image for that pixel.

In the case in which the dynamic image of the chest is an image radiographed under respiratory conditions, the change over time in the signal value for each of the pixels that correspond to each other between frame images may be filtered by applying a high-pass filter (for example, a filter with a cutoff frequency of 0.7 Hz) in the time direction before calculating the analysis reference frame image and the difference values. With this arrangement, low-frequency signal variations due to ventilation can be removed, and the change over time in the signal values due to blood flow can be extracted.

Note that the types and methods of dynamic analysis performed by the dynamic analysis WS 22 are not limited to the above-described.

The terminal apparatus 23 is a computer in which the medical collaboration program is installed for using the medical collaboration service provided by the cloud server 30. Namely, the terminal apparatus 23 is a computer provided with a controller including a CPU, RAM, and/or the like, storage, an input device, a display, and a communicator, the computer being for receiving examination request information from the cloud server 30, creating a radiology report by a physician referring to a dynamic image and a dynamic analysis image generated on the basis of the examination request information, accessing the cloud server 30 through the communication network N, and transmitting (uploading) the dynamic image, the dynamic analysis image, and the radiology report to the cloud server 30.

Note that the terminal apparatus 23 may also be integrated with a radiology terminal or the like, not illustrated, of the PACS 24.

The PACS 24 saves and manages medical images radiographed inside the medical facility B.

The HIS 25 issues and transmits examination order information to the radiographic apparatus 21 and the dynamic analysis WS 22. Note that the configuration may also be provided with a radiology information system (RIS) instead of the HIS 25.

[Configuration of Cloud Server 30]

The cloud server 30 is an image management server that provides a medical collaboration service to registered medical facilities and manages information about examination requests between medical facilities and examination result data acquired through examinations (in the present embodiment, dynamic images, dynamic analysis images, and radiology reports).

Figure 3:
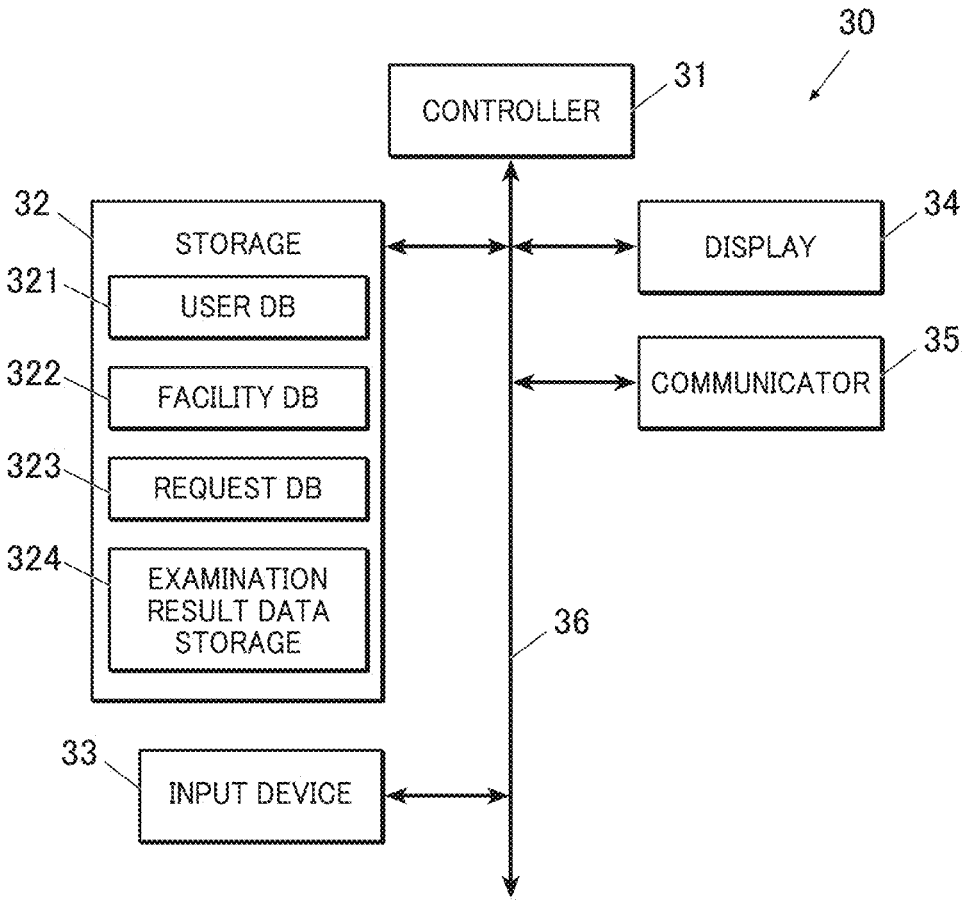
FIG. 3 is a block diagram illustrating a functional configuration of a cloud server in FIG. 1.

FIG. 3 is a block diagram illustrating a functional configuration of the cloud server 30. As illustrated in FIG. 3, the cloud server 30 is provided with a controller 31 (hardware processor), storage 32, an input device 33, a display 34, and a communicator 35, the above being connected by a bus 36.

The controller 31 includes a CPU, RAM, and/or the like. The CPU of the controller 31, in response to an operation performed on the input device 33, reads out a system program and any of various processing programs stored in the storage 32, loads the programs into the RAM, and centrally controls operations by each component of the cloud server 30 according to the loaded programs. The controller 31 also executes the processing and the like on the cloud server 30 side illustrated in FIG. 4 according to a program stored in the storage 32.

The storage 32 includes a non-volatile semiconductor memory, a hard disk, and/or the like. The storage 32 stores various programs to be executed by the controller 31, parameters necessary for the execution of processing by the programs, and/or data such as processing results. For example, the storage 32 stores a service-providing program A (a program for executing the processing on the cloud server 30 side illustrated in FIG. 4) for providing the medical collaboration service. The various programs are stored in the form of readable program code, and the controller 31 sequentially executes operations in accordance with the program code.

Additionally, the storage 32 includes a user database (DB) 321, a facility DB 322, a request DB 323, and examination result data storage 324.

The user DB 321 stores user information related to a user (physician) who can use the medical collaboration service provided by the cloud server 30. For example, the user DB 321 is provided with items for identifying the user, such as "User ID", "Login Password", "Physician Name" (username), "Address", "Telephone Number", "Email Address", "Folder Path", and the "Facility ID", "Facility Name", and "Department" of the medical facility to which the user belongs, and the user DB 321 stores the data of user information including the information of the above items.

The storage 32 in this case is provided with the examination result data storage 324 including a folder for each user for storing examination result data such as a dynamic image, a dynamic analysis image, and a radiology report transmitted from the medical facility B according to an examination request from a user at the medical facility A. The "Folder Path" included in the user information is information indicating a path to a folder (the location of a folder) for that user.

The facility DB 322 stores facility information related to medical facilities (the medical facilities A and B) that can use the medical collaboration service provided by the cloud server 30. For example, the facility DB 322 is provided with items for identifying the medical facility, such as "Facility ID", "Facility Name", "Facility Address", "Main Telephone Number", and "Examination Type", and the facility DB 322 stores facility information including the information of the above items. The "Examination Type" indicates the type of examination for which the facility will accept an examination request.

The request DB 323 stores examination request information related to an examination request received from the medical facility A. For example, the request DB 323 is provided with items for identifying the request, such as "Request ID", "Requesting User ID", "Requesting Facility ID", "Requesting Patient Information", "Requested Facility ID", "Requested Examination Type", "Request Details", "Request Date/Time", "Folder Path", and "File Path" (the file paths to each of the radiology report, the dynamic image, and the dynamic analysis image), and the request DB 323 stores examination request information including the information of the above items. The "Requesting Patient Information" indicates information about the patient to be examined, such as the patient's name, date of birth, age, sex, and a patient ID at the medical facility to which the requesting user belongs. The "Request Details" indicates details about the examination, such as the radiography area and the type of dynamic analysis. The "Folder Path" is information indicating a path to a folder (the location of a folder) where examination result data for the request is stored. The "File Path" is information indicating the respective storage locations of the radiology report, the dynamic image, and the dynamic analysis image.

The examination result data storage 324 stores examination result data such as a dynamic image, a dynamic analysis image, and a radiology report transmitted from the medical facility B according to an examination request from a user. The examination result data storage 324 has a folder for each examination request inside the folder for each user, and the examination result data is stored in the folder corresponding to the request ID of the examination request inside the folder of the user requesting the examination. Each folder is accessible only by the user corresponding to that folder.

The input device 33 is provided with a keyboard furnished with cursor keys, numerical input keys, any of various types of function keys, and the like, and a pointing device such as a mouse, and outputs to the controller 31 an instruction signal inputted by a key operation on the keyboard and/or a mouse operation. The input device 33 may also be provided with a touch panel on the display screen of the display 34, and in this case the input device 33 outputs to the controller 31 an instruction signal inputted through the touch panel.

The display 34 includes a monitor such as a liquid crystal display (LCD) panel or a cathode-ray tube (CRT) monitor and displays an input instruction from the input device 33, data, and/or the like according to the instruction of a display signal inputted from the controller 31.

The communicator 35 transmits and receives various data to and from external equipment connected to the communication network N.

[Operations by Image Management System 100]

Next, operations by the image management system 100 will be described.

The medical facility A lacks a radiographic apparatus capable of dynamic radiography, and thus cannot conduct an examination by dynamic radiography. Accordingly, when a patient requiring dynamic radiography is admitted, a physician at the medical facility A contacts (or has a medical staff member contact) a physician in charge at the medical facility B, which has a radiographic apparatus capable of dynamic radiography, and reserves an appointment date for an examination by dynamic radiography. Thereafter, the cloud server 30 is accessed, and the series of processes illustrated in FIG. 4 is initiated.

Figure 4:
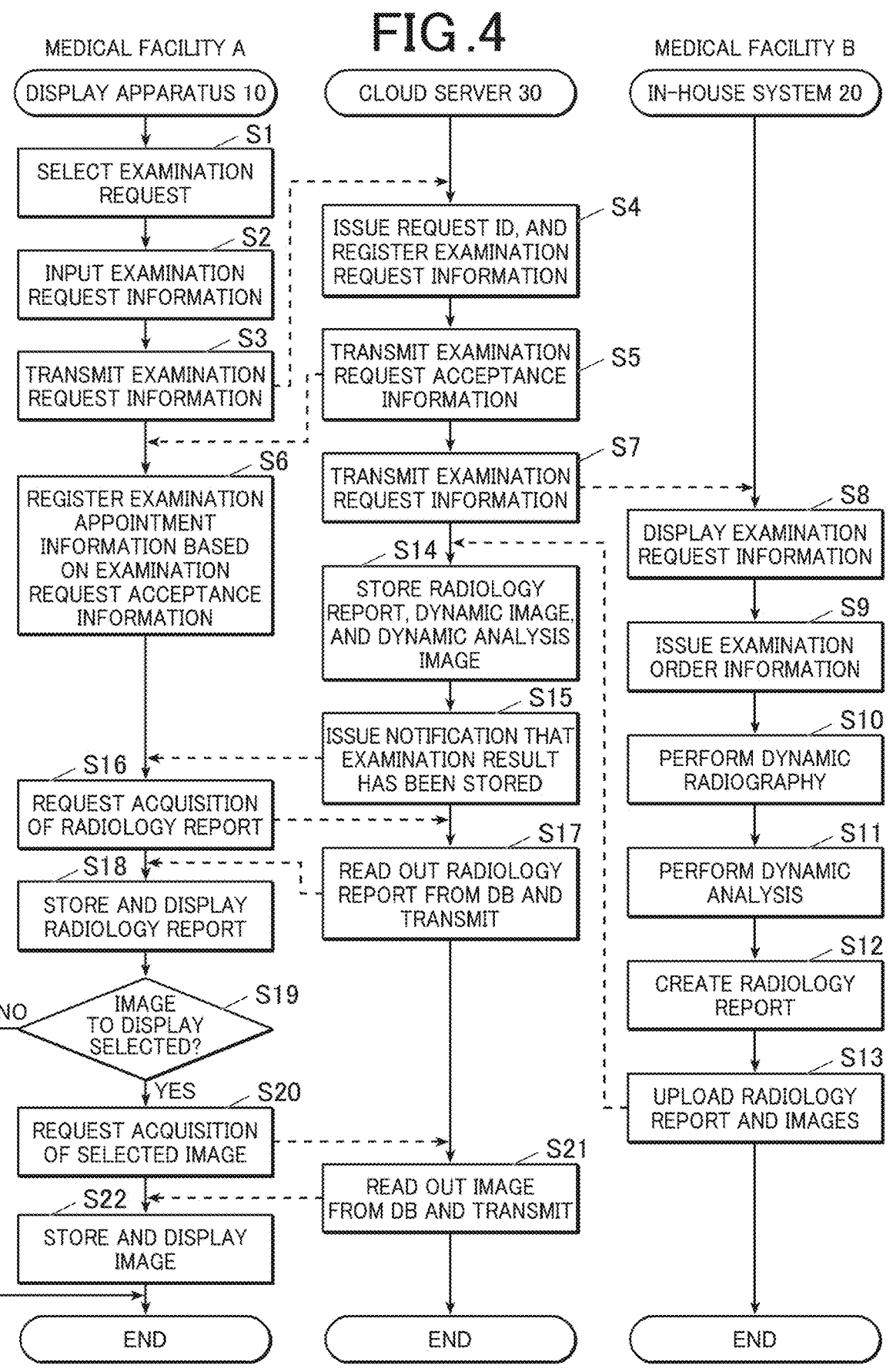
FIG. 4 is a diagram illustrating a flow of processing in the image management system in FIG. 1 for a case in which a physician at a medical facility A requests an examination by dynamic radiography at a medical facility B and acquires examination result data through a cloud server.

FIG. 4 is a diagram illustrating a flow of processing in the image management system 100 for the case in which the physician at the medical facility A requests an examination by dynamic radiography at the medical facility B and acquires examination result data through the cloud server 30. The processing by the display apparatus 10 in FIG. 4 is executed through the cooperation of the controller 11 of the display apparatus 10 and the medical collaboration program stored in the storage 12. The processing by the cloud server 30 is executed through the cooperation of the controller 31 and the service-providing program A stored in the storage 32. The processing by the in-house system 20 is executed by the apparatus forming the in-house system 20.

Note that when a user operating the display apparatus 10 or the terminal apparatus 23 uses the medical collaboration service provided by the cloud server 30, the user is required to perform login authentication, but the following description assumes that the login authentication has already been performed.

In the display apparatus 10, when an examination request is selected by an operation performed on the input device 13 by the user (the physician at the medical facility A) from a menu screen of the medical collaboration service (step S1), the controller 11 causes the display 14 to display an examination request screen (not illustrated) for inputting information requesting an examination and accepts examination request information inputted through the input device 13 (step S2).

In step S2, the input of information such as the facility ID and the facility name of the recipient (that is, the medical facility B) of the request for an examination, patient information about the patient to be examined, such as the patient ID (a patient ID in the medical facility A) and the patient's name, date of birth, sex, and age, the requested examination type, the request details, and the examination appointment date are accepted, for example. At this point, the user inputs dynamic radiography as the examination type.

Note that the information in some items of the examination request information, such as the examination type and the request details, may also be selectable from a plurality of candidates.

When the examination request information is inputted and a transmit instruction is given through the input device 13, the controller 11 adds the request date and time (the current date and time), information about the requesting user (the user ID of the login user), and the like to the inputted examination request information, and transmits the combined information to the cloud server 30 through the communicator 15 (step S3).

In the cloud server 30, when the examination request information is received by the communicator 35, the controller 31 issues a request ID, creates a folder for storing the examination result data of the examination corresponding to the request ID inside the folder of the requesting user in the examination result data storage 324, and registers the content of the received examination request information and the folder path of the created folder in the request DB 323 in association with the issued request ID (step S4). Additionally, the controller 31 transmits examination request acceptance information to the display apparatus 10 through the communicator 35 (step S5).

The examination request acceptance information is information that includes the request ID and the accepted examination request information, for example.

The controller 11 of the display apparatus 10, upon receiving the examination request acceptance information from the cloud server 30, generates examination appointment information based on the examination request acceptance information, stores the examination appointment information in the storage 12, and causes the display 14 to display the examination appointment information (step S6).

In step S6, the controller 11 generates examination appointment information including patient information and examination information about the requested examination, on the basis of the patient information, the requested examination type, the request details, the examination appointment date, and the like in the examination request acceptance information. The request ID included in the examination request acceptance information is included in the examination appointment information.

Also, for example, the physician at the medical facility A outputs the examination request acceptance information using a printer or the like, hands over the examination request acceptance information to the patient and requests the patient to undergo an examination at the medical facility B on the examination appointment date.

The controller 31 of the cloud server 30 transmits the examination request information to the terminal apparatus 23 of the requested medical facility B through the communicator 35 (step S7).

The terminal apparatus 23 of the medical facility B receives and stores the examination request information in storage and displays the examination request information on a display (step S8).

This arrangement makes it possible to confirm the details of the examination request at the medical facility B.

Next, in the HIS 25, examination order information is issued on the basis of the examination request information (step S9).

For example, a physician or the like who has confirmed the examination request details inputs the examination order information based on the examination request information into the HIS 25, thereby causing the examination order information to be issued. At this time, the request ID is inputted into a prescribed item (for example, comments) of the examination order information. The HIS 25 issues and transmits the examination order information associated with the request ID to the radiographic apparatus 21 and the dynamic analysis WS 22.

When a patient carrying examination request acceptance information visits the medical facility B on the examination appointment date, dynamic radiography is performed on a subject area of the patient (examinee) by the radiographic apparatus 21 of the medical facility B on the basis of the examination order information corresponding to the examination request information, and the obtained dynamic image is transmitted to the dynamic analysis WS 22 (step S10).

In the header of the dynamic image acquired by dynamic radiography, the radiographic apparatus 21 writes and adds not only patient information, examination information, and image identification information for identifying the dynamic image, but also the request ID in the prescribed item of the examination order information. Also, in the header of each frame image of the dynamic image, the radiographic apparatus 21 additionally writes and adds a frame number indicating the radiographic sequence.

The dynamic analysis WS 22, upon receiving the dynamic image, generates a dynamic analysis image by performing dynamic analysis on the dynamic image acquired by radiography on the basis of the type of dynamic analysis included in the examination order information, and transmits the dynamic image and the dynamic analysis image to the terminal apparatus 23 (step S11).

For example, in the case of receiving a dynamic image of the chest, the dynamic analysis WS 22 performs ventilatory analysis and/or blood flow analysis and generates a ventilatory analysis image and/or a blood flow analysis image. Thereafter, for example, the dynamic analysis WS 22 adds supplementary information similar to the dynamic image serving as the basis of analysis to the header of the generated dynamic analysis image and transmits the dynamic analysis image together with the dynamic image to the PACS 24 to be saved in the PACS 24, and also transmits the images to the terminal apparatus 23.

In response to a user operation, the terminal apparatus 23 creates a radiology report based on the dynamic image and the dynamic analysis image transmitted from the dynamic analysis WS 22 (step S12).

The radiologist of the dynamic image refers to the dynamic image and the dynamic analysis image generated on the basis of the examination request information and creates a radiology report on the terminal apparatus 23.

Information such as findings, a diagnostic result, and comments can be inputted into the radiology report created in the present embodiment, and in addition, a thumbnail image of one or multiple frame images of the dynamic image or the dynamic analysis image (or both) can be attached to the radiology report.

For example, on a report creation screen (not illustrated) of the terminal apparatus 23, the dynamic image and the dynamic analysis image generated on the basis of the examination request information are displayed, and when the radiologist uses an input device to select one or multiple frame images of the dynamic image or the dynamic analysis image determined to be useful for diagnosis (used in the diagnosis) from among the displayed images, the terminal apparatus 23 reduces the selected frame images to generate thumbnail images, and attaches the generated thumbnail images to the radiology report. Information for identifying the frame images attached to the radiology report (such as the request ID, image identification information, and frame numbers, for example) is stored in the radiology report in association with each thumbnail image.

Figure 5:
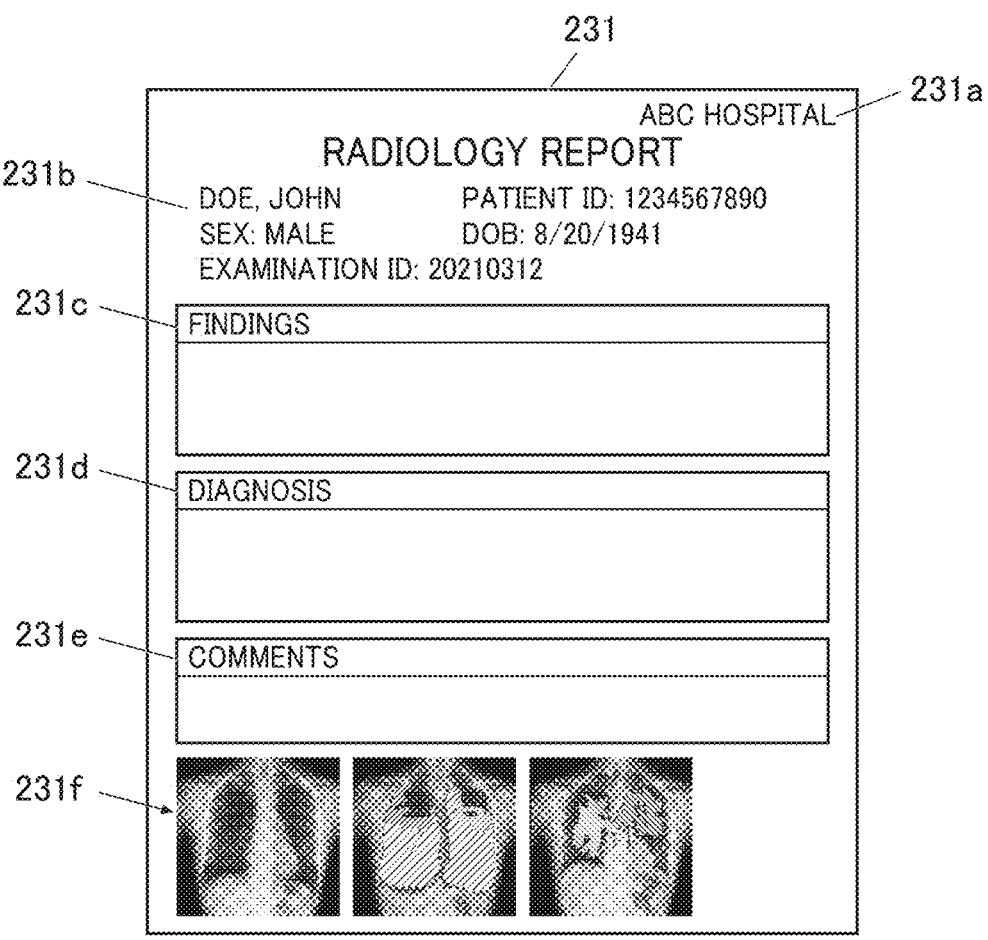
FIG. 5 is a diagram illustrating an example of a radiology report.

FIG. 5 is a diagram illustrating an example of a radiology report 231 created in step S12. As illustrated in FIG. 5, the radiology report 231 is provided with the facility name 231a of the medical facility where the examination was conducted, patient information 231b, a findings field 231c, a diagnostic result field 231d, a comments field 231e, and an image attachment field 231f.

As illustrated in FIG. 5, one or multiple frame images needed for diagnosis and selected from the dynamic image or the dynamic analysis image are attached to the radiology report 231 as thumbnail images, and therefore the requesting physician is able to check the images needed for diagnosis on the radiology report. In particular, by attaching a dynamic analysis image (for example, a ventilatory analysis image or a blood flow analysis image) to the radiology report, the physician can easily check the patient's ventilatory functions, blood flow functions, and the motion of the subject area on the radiology report, for example.

Note that in the case in which a plurality of frame images are attached to the radiology report, thumbnail images of the plurality of frame images forming the dynamic image or the dynamic analysis image may be attached side by side. With this arrangement, the requesting physician is able to check each of the plurality of frame images forming the dynamic image or the dynamic analysis image on the radiology report. Alternatively, the thumbnail images of the dynamic image or the dynamic analysis image may be attached as a video.

When report creation is finished, the terminal apparatus 23 uploads the created radiology report, the dynamic image, and the dynamic analysis image to the cloud server 30 in association with the request ID of the examination (step S13).

In the cloud server 30, when the radiology report, the dynamic image, and the dynamic analysis image are received from the terminal apparatus 23 through the communicator 35, the controller 31 references the request DB 323 and causes the received radiology report, dynamic image, and dynamic analysis image to be stored in the folder of the request ID corresponding to the received radiology report, dynamic image, and dynamic analysis image (step S14).

The controller 31 registers the storage location (file path) of each of the radiology report, the dynamic image, and the dynamic analysis image in the record, in the request DB 323, of the request ID corresponding to the received radiology, dynamic image, and dynamic analysis image.

The controller 31 also transmits, through the communicator 35, notification information notifying the display apparatus 10 of the requesting user that examination result data for the examination request has been stored (step S15).

For example, the controller 31 transmits notification information which notifies the display apparatus 10 that examination result data for the examination request has been stored in the cloud server 30 and which notifies information (such as an URL) indicating the storage location of the radiology report among the examination result data.

When the patient visits the medical facility A for a follow-up on a later date or the like, the user receiving the notification information issues a radiology report download request from the display apparatus 10 to the cloud server 30.

In the display apparatus 10, when the storage location of the radiology report is specified and an instruction to download the radiology report is given through the input device 13, the controller 31 issues to the cloud server 30 a download request (acquisition request) for the radiology report stored in the specified storage location (step S16).

The cloud server 30 reads out the radiology report from the specified storage location in the examination result data storage 324, associates the request ID with the read-out radiology report, and transmits the radiology report to the display apparatus 10 through the communicator 35 (step S17).

In the display apparatus 10, when the radiology report is received from the cloud server 30 through the communicator 15, the controller 31 stores the received radiology in the storage 12 in association with the examination appointment information (patient information and examination information) including the request ID associated with the received radiology report and causes the display 14 to display the radiology report (step S18).

In this way, the radiology report received from the cloud server 30 can be automatically linked on the basis of the request ID to the examination appointment information previously registered in the display apparatus 10, thereby eliminating the burden of the user having to associate the downloaded radiology report by specifying which examination appointment information in the medical facility A the radiology report corresponds to.

In step S18, as illustrated in FIG. 5, the radiology report with attached thumbnail images of the dynamic image or the dynamic analysis image is displayed on the display 14.

At this point, a problem may occur in which the dynamic image or the dynamic analysis image contains a large amount of data, and as such, if all frame images of the dynamic image or the dynamic analysis image are downloaded directly to a low-performance display apparatus, the download may be time-consuming, the display apparatus may freeze, and the downloaded data may occupy much of the storage capacity. For this reason, displaying and checking the dynamic image and the dynamic analysis image is time-consuming. In the present embodiment, a radiology report with one or multiple attached frame images of the dynamic image or the dynamic analysis image that have been reduced for reference is downloaded, and therefore the download can be completed in a short time, thereby making it possible to display and check the dynamic image and the dynamic analysis image efficiently.

When one of the frame images attached to the displayed radiology report is selected using the input device 13 (step S19; YES), the controller 11 transmits an acquisition request for the image data of the selected frame image to the cloud server 30 through the communicator 15 (step S20).

For example, the controller 11 transmits to the cloud server 30 an acquisition request for information identifying the selected frame image (such as, for example, the request ID and an image identification number of the dynamic image (or the dynamic analysis image) and the frame number of the selected frame image, or the request ID and information indicating the position of the selected frame image in the radiology report) and the frame image itself.

In the cloud server 30, when an acquisition request for a frame image is received from the display apparatus 10 through the communicator 35, the controller 31 reads out the frame image requested by the display apparatus 10 from the examination result data storage 324 and transmits the read-out frame image to the display apparatus 10 through the communicator 35 (step S21).

The controller 11 of the display apparatus 10, upon receiving the image data of the frame image from the cloud server 30 through the communicator 15, stores the received frame image in the storage 12 in association with the examination appointment information (patient information and examination information) including the request ID associated with the received frame image, and causes the display 14 to display the received frame image (step S22).

In this way, in the display apparatus 10, only the image data of a frame image that the user has determined to be needed is downloaded and displayed from among the frame images forming the dynamic image or the dynamic analysis image attached as thumbnail images to the radiology report, thereby making it possible to acquire the needed image efficiently in a short data acquisition time. Moreover, the frame image received from the cloud server 30 is automatically linked on the basis of the request ID to the examination appointment information previously issued in the display apparatus 10, thereby eliminating the burden of the user having to associate the downloaded frame image by specifying which examination appointment information in the medical facility A the frame image corresponds to.

Note that in the above embodiment, a radiology report is downloaded to the display apparatus 10 according to an instruction from the user, but the controller 11 of the display apparatus 10 may also check the examination result data storage 324 of the cloud server 30 periodically in the background and download the radiology report automatically.

Second Embodiment

Next, a second embodiment of the present invention will be described.

In the image management system 100 according to the second embodiment, a web browser is installed in the display apparatus 10, and the transmission and reception of data between the display apparatus 10 requesting an examination and the cloud server 30 is performed via a web screen provided to the display apparatus 10 from the cloud server 30. Otherwise, since the configuration of the image management system 100 according to the second embodiment is similar to what is described in the first embodiment, the description is incorporated herein, and operations by the image management system 100 according to the second embodiment are described below.

The medical facility A lacks a radiographic apparatus capable of dynamic radiography, and thus cannot conduct an examination by dynamic radiography. Accordingly, when a patient requiring dynamic radiography is admitted, a physician at the medical facility A contacts (or has a medical staff member contact) a physician in charge at the medical facility B, which has a radiographic apparatus capable of dynamic radiography, and reserves an appointment date for an examination by dynamic radiography. Thereafter, the cloud server 30 is accessed, and the series of processes illustrated in FIG. 6 is initiated.

Figure 6:
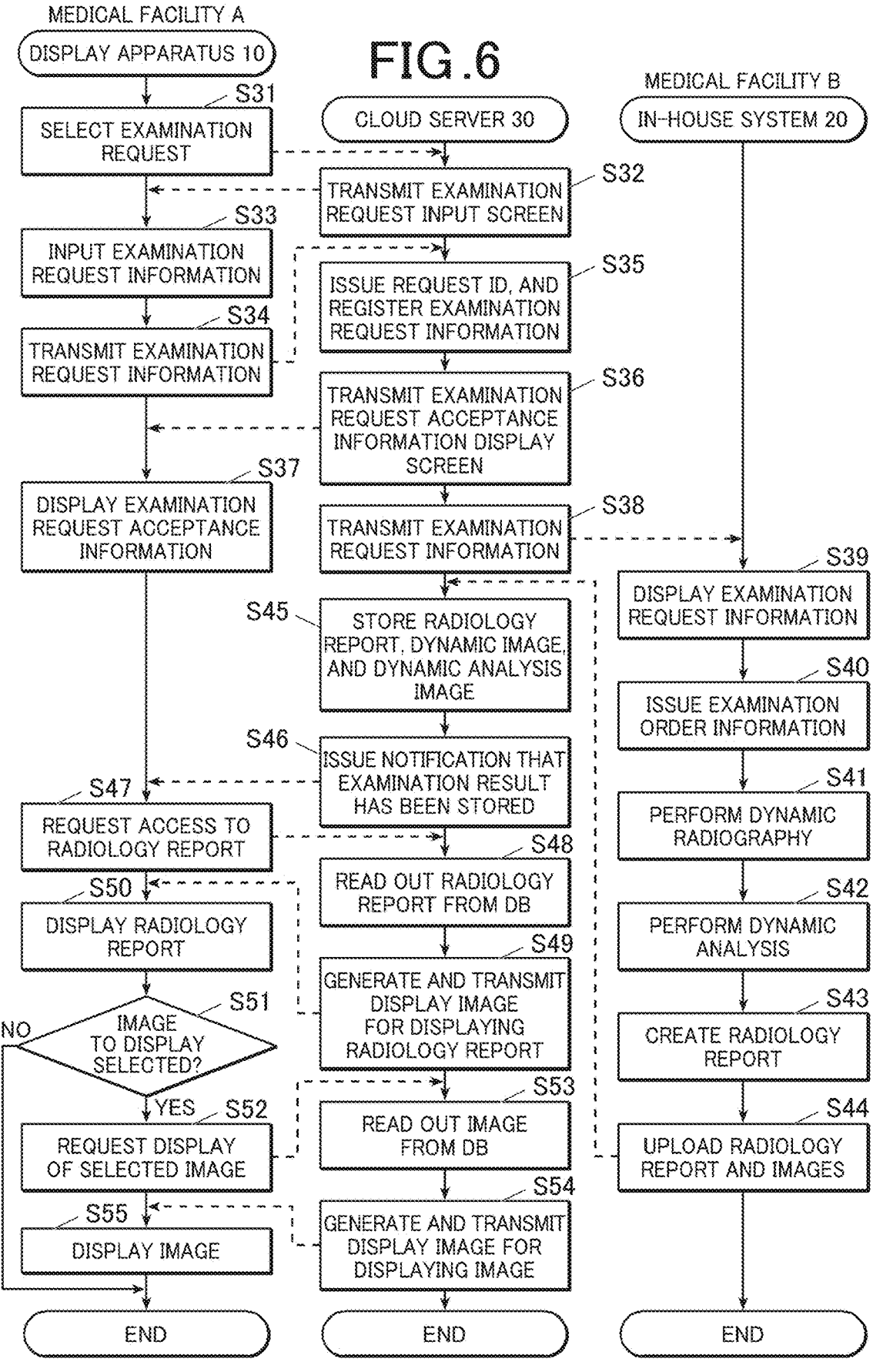
FIG. 6 is a diagram illustrating a flow of processing in an image management system according to a second embodiment for the case in which the physician at the medical facility A requests an examination by dynamic radiography at the medical facility B and displays examination result data through a cloud server.

FIG. 6 is a diagram illustrating a flow of processing in the image management system 100 according to the second embodiment for the case in which the physician at the medical facility A requests an examination by dynamic radiography at the medical facility B and acquires examination result data. The processing by the display apparatus 10 in FIG. 6 is executed through the cooperation of the controller 11 of the display apparatus 10 and a web browser stored in the storage 12. The processing by the cloud server 30 is executed through the cooperation of the controller 31 and the service-providing program stored in the storage 32. The processing by the in-house system 20 is executed by the apparatus forming the in-house system 20. By executing the processing illustrated in FIG. 6, the cloud server 30 functions as an acquirer and an image generator of an image management server according to the present invention.

Note that when a user operating the display apparatus 10 or the terminal apparatus 23 uses the medical collaboration service provided by the cloud server 30, the user is required to perform login authentication, but the following description assumes that the login authentication has already been performed.

In the display apparatus 10, when an examination request is selected by an operation performed on the input device 13 from a menu screen transmitted from the cloud server 30 after login authentication is finished (step S31), the controller 31 of the cloud server 30 transmits an examination request input screen to the display apparatus 10 through the communicator 35 (step S32).

In the display apparatus 10, the controller 11 displays the received examination request input screen on the display 14 and accepts the input of examination request information through the input device 13 (step S33), adds the request date and time (the current date and time), information about the requesting user (the user ID of the login user), and the like to the inputted examination request information, and transmits the combined information to the cloud server 30 through the communicator 15 (step S34).

Since the content inputted in step S33 is similar to what is described in step S2 of FIG. 4, the description is incorporated herein.

In the cloud server 30, when the examination request information is received by the communicator 35, the controller 31 issues a request ID, creates a folder for storing the examination result data of the examination corresponding to the request ID inside the folder of the requesting user in the examination result data storage 324, and registers, in association with the issued request ID, the content of the received examination request information and the folder path of the created folder in the request DB 323 (step S35). Additionally, the controller 31 transmits a display screen of examination request acceptance information to the display apparatus 10 through the communicator 35 (step S36).

The examination request acceptance information is information that includes the request ID and the examination request information, for example.

The controller 11 of the display apparatus 10, upon receiving the display screen of the examination request acceptance information from the cloud server 30, causes the display 14 to display the examination request acceptance information (step S37).

For example, the physician at the medical facility A outputs the examination request acceptance information using a printer or the like, hands over the examination request acceptance information to the patient and requests the patient to undergo an examination at the medical facility B on the examination appointment date.

The controller 31 of the cloud server 30 transmits the examination request information to the terminal apparatus 23 of the requested medical facility B through the communicator 35 (step S38).

The terminal apparatus 23 of the medical facility B executes the processing in steps S39 to S44, creates a radiology report based on the examination request information, and uploads the radiology report, the dynamic image, and the dynamic analysis image to the cloud server 30 in association with the request ID of the examination (step S44).

Since the processing in steps S39 to S44 is similar to what is described in steps S8 to S13 of FIG. 4, the description is incorporated herein.

In the cloud server 30, when the radiology report, the dynamic image, and the dynamic analysis image are received from the terminal apparatus 23 through the communicator 35, the controller 31 references the request DB 323 and causes the received radiology report, dynamic image, and dynamic analysis image to be stored in the folder of the request ID corresponding to the received radiology report, dynamic image, and dynamic analysis image (step S45).

The controller 31 registers the storage location (file path) of each of the radiology report, the dynamic image, and the dynamic analysis image in the record, in the request DB 323, of the request ID corresponding to the received radiology, dynamic image, and dynamic analysis image.

The controller 31 also transmits, through the communicator 35, notification information notifying the display apparatus 10 of the requesting user that examination result data for the examination request has been stored (step S46).

For example, the controller 31 transmits notification information which notifies the display apparatus 10 that examination result data for the examination request has been stored in the cloud server 30 and which notifies information (such as an URL) indicating the storage location of the radiology report among the examination result data.

When the patient visits the medical facility A for a follow-up on a later date or the like, the user receiving the notification information issues a request to access the radiology report from the display apparatus 10 to the cloud server 30 on the basis of the notification information (step S47).

The controller 31 of the cloud server 30 reads out the radiology report from the specified storage location in the examination result data storage 324 (step S48), generates a display image (in the present embodiment, a web screen displaying the radiology report) for displaying the read-out radiology report on the display 14 of the display apparatus 10, and transmits the display image to the display apparatus 10 through the communicator 35 (step S49).

In the display apparatus 10, when the display image of the radiology report is received from the cloud server 30 through the communicator 15, the controller 11 causes the display 14 to display the radiology report on the basis of the received display image (step S50).

In step S50, as illustrated in FIG. 5, the radiology report with attached thumbnail images of the dynamic image or the dynamic analysis image is displayed on the display 14.

At this point, a problem may occur in which the dynamic image or the dynamic analysis image contains a large amount of data, and as such, if all frame images of the dynamic image or the dynamic analysis image are downloaded directly to a low-performance display apparatus, the download may be time-consuming, the display apparatus may freeze, and the downloaded data may occupy much of the storage capacity. For this reason, displaying and checking the dynamic image and the dynamic analysis image is time-consuming. In the present embodiment, a display image (for example, a web screen) of the radiology report with one or multiple attached frame images of the dynamic image or the dynamic analysis image is created in the cloud server 30 (server-side rendering) and transmitted to the display apparatus 10, thereby making it possible to display and check the radiology report, the dynamic image, and the dynamic analysis image efficiently on the display apparatus 10 without downloading.

When a frame image to be displayed is selected using the input device 13 from among the frame images attached to the radiology report displayed on the display 14 (step S51; YES), the controller 11 transmits a display request for the selected frame image to the cloud server 30 through the communicator 15 (step S52).

In the cloud server 30, when a display request for a frame image is received from the display apparatus 10 through the communicator 35, the controller 31 retrieves the frame image requested by the display apparatus 10 from the examination result data storage 324 (step S53), generates a display image (in the present embodiment, a web screen displaying the frame image) for displaying the retrieved frame image on the display 14 on the display apparatus 10, and transmits the generated display image to the display apparatus 10 through the communicator 35 (step S54).

In the display apparatus 10, when the display image of the frame image is received from the cloud server 30 through the communicator 15, the controller 11 causes the display 14 to display the received display image of the frame image (step S55).

In this way, the cloud server 30 creates and transmits to the display apparatus 10 a display image of the image data of a frame image that the user has determined to be needed from among the frame images forming the dynamic image or the dynamic analysis image attached as thumbnail images to the radiology report, thereby making it possible to display, check, and refer to the dynamic image and the dynamic analysis image needed for diagnosis efficiently on the display apparatus 10 without downloading.

Note that a configuration allowing the radiology report and the displayed frame image to be downloaded to the display apparatus 10 is also possible. For example, a configuration is possible in which the controller 31 of the cloud server 30 selects a frame image requested for display by the display apparatus 10 as a frame image to be transmitted to the display apparatus 10 from among the frame images attached to the radiology report, acquires the selected frame image from the examination result data storage 324, and transmits the acquired frame image to the display apparatus 10 through the communicator 35.

As described above, the controller 11 of the display apparatus 10 of the image management system 100 acquires from the cloud server 30 through the communicator 15, a radiology report to which a dynamic image acquired by irradiating and dynamically radiographing a subject with radiation or a dynamic analysis image indicating a result of analyzing the dynamic image is attached and displays the acquired radiology report.

For example, the controller 11 acquires from the cloud server 30 a radiology report with attached thumbnails of the dynamic image or the dynamic analysis image.

Consequently, the dynamic image and the dynamic analysis image can be downloaded (acquired) in a short time, thereby making it possible to address the problems of the related art, such as the download of the dynamic image or the dynamic analysis image being time-consuming, the display apparatus freezing, and the downloaded data occupying much of the storage capacity and making it possible to display the dynamic image and the dynamic analysis image efficiently.

In another example, the controller 11 acquires from the cloud server 30 a radiology report with one attached frame image from among the plurality of frame images forming the dynamic image or the dynamic analysis image and displays the acquired radiology report.

Consequently, a radiology report with only a single, major frame image attached is acquired from the cloud server 30, thereby making it possible to download (acquire) the dynamic image or the dynamic analysis image in a short time and display the dynamic image and the dynamic analysis image efficiently.

In another example, the controller 11 acquires from the cloud server 30 a radiology report with a plurality of frame images forming the dynamic image or the dynamic analysis image attached side by side.

Consequently, a radiology report with some or all of the plurality of frame images forming the dynamic image, or the dynamic analysis image attached side by side is acquired from the cloud server 30, thereby making it possible to download (acquire) the dynamic image or the dynamic analysis image in a short time, and display the dynamic image and the dynamic analysis image efficiently and in an easy-to-see way.

Also, when the user uses the input device 13 to select a frame image to be acquired from among the plurality of frame images forming the dynamic image or the dynamic analysis image attached to the radiology report, the controller 11 acquires the selected frame image from the cloud server 30 and causes the display 14 to display the acquired frame image.

Consequently, a frame image selected by the user from among the frame images attached to the radiology report can be acquired and displayed, thereby enabling the user to acquire and check a needed image.

Moreover, the controller 11 acquires and displays a radiology report with the dynamic analysis image attached, thereby enabling the user to easily check a patient's ventilatory functions, blood flow functions, and the motion of the subject area on the radiology report, for example.

Also, the cloud server 30 comprises the storage 32 that stores a radiology report to which a dynamic image acquired by irradiating and dynamically radiographing a subject with radiation or a dynamic analysis image indicating a result of analyzing the dynamic image is attached, and the controller 31 acquires the radiology report from the storage 32, generates a display image for displaying the acquired radiology report on the display 14 of the display apparatus 10, and transmits the generated display image to the display apparatus 10.

Consequently, since a display image to be displayed on the display 14 of the display apparatus 10 is generated in the cloud server 30, only the data necessary for displaying may simply be downloaded, without downloading the full-sized dynamic image or dynamic analysis image to the display apparatus 10, thereby making it possible to display the dynamic image or the dynamic analysis image efficiently on the display apparatus 10.

Note that the content described in the above embodiments indicates preferred examples of a dynamic analysis system according to the present invention, and the present invention is not limited to these examples.

For example, in the above embodiments, the case in which the image management system 100 is a system for medical collaboration between medical facilities and the image management server is a cloud-based image management server is described by way of example, but the image management system 100 may also be an image management system set up inside a medical facility and the image management server may also be an image management server provided inside the medical facility (connected to the display apparatus 10 through an in-house communication network).

Moreover, in the second embodiment, interactions between the cloud server 30 and the terminal apparatus 23 may also be performed using a web application.

Also, in the above embodiments, one or a plurality of frame images forming the dynamic image or the dynamic analysis image that have been selected (determined to be important for diagnosis) in the medical facility B are attached to the radiology report, but information such as a flag indicating that the display priority is high may also be added to the header or the like of one or a plurality of frame images that have been determined to have a high display priority in the medical facility B, and in the display apparatus 10, only a frame image with added information indicating that the display priority is high can be acquired from the cloud server 30, thereby shortening the time associated with downloading.

In the above description, the example is disclosed where the hard disk, the semiconductor nonvolatile memory or the like is used as a computer-readable medium for the program according to the present invention. However, there is no limitation to this example. As another computer-readable medium, a portable recording medium, such as a CD-ROM, may be applied. Carrier waves are also applicable as a medium of providing data on the program according to the present invention via a communication line.

Other details of the configuration and operation of each apparatus forming an image management system can also be modified, as appropriate, without departing from the gist of the invention.

The present embodiment enables the efficient display, on a display apparatus, of a dynamic image and a dynamic analysis image stored in an external apparatus such as an image management server.

Although embodiments of the present invention have been described and illustrated in detail, the disclosed embodiments are made for purposes of illustration and example only and not limitation. The scope of the present invention should be interpreted by terms of the appended claims.

The invention claimed is:

1. A display apparatus for display of a dynamic radiographic image comprising:
a hardware processor disposed at a first location that requests and acquires, from an external apparatus disposed at a second location remotely located from the first location, a radiology report to which one or more thumbnails based on at least a part of a dynamic image acquired by irradiating and dynamically radiographing a subject with radiation at the second location or a dynamic analysis image indicating a result of analyzing the dynamic image is attached; and
a display at the first location that displays the acquired radiology report acquired by the hardware processor,
wherein the hardware processor selects one thumbnail from the one or more thumbnails, and transmits an acquisition request for the dynamic image or the dynamic analysis image serving as a source of the selected thumbnail to the external device, and acquires the dynamic image or the dynamic analysis image serving as a source of the selected thumbnail from the external device that has responded to the acquisition request, wherein the display displays the dynamic image or the dynamic analysis image corresponding to the one image acquired.

2. The display apparatus according to claim 1, wherein a plurality of frame images forming the dynamic image, or the dynamic analysis image are attached side by side to the radiology report.

3. The display apparatus according to claim 1, wherein one frame image from among a plurality of frame images forming the dynamic image or the dynamic analysis image is attached to the radiology report.

4. The display apparatus according to claim 1, wherein the hardware processor selects a frame image to be acquired from among a plurality of frame images forming the dynamic image or the dynamic analysis image attached to the radiology report and acquires the selected frame image from the external apparatus, and the display displays the acquired frame image.

5. The display apparatus according to claim 1, wherein the radiology report is a radiology report with the dynamic analysis image attached.

6. The display apparatus according to claim 5, wherein the dynamic analysis image is an image obtained by analyzing motion of the subject in the dynamic image.

7. The display apparatus according to claim 6, wherein the dynamic analysis image is a ventilatory analysis image or a blood flow analysis image.

8. An image management server comprising:

storage that stores a radiology report to which one or more thumbnails based on at least a part of a dynamic image acquired by irradiating and dynamically radiographing a subject with radiation or a dynamic analysis image indicating a result of analyzing the dynamic image is attached; and a hardware processor disposed at a first location that acquires the radiology report from the storage disposed at a second location remotely located from the first location, and generates a display image for displaying the acquired radiology report on an external display apparatus;

wherein the hardware processor selects one thumbnail from the one or more thumbnails, and transmits an acquisition request for the dynamic image or the dynamic analysis image serving as a source of the selected thumbnail to the external device, and acquires the dynamic image or the dynamic analysis image serving as a source of the selected thumbnail from the external device that has responded to the acquisition request, wherein the display displays the dynamic image or the dynamic analysis image corresponding to the one image acquired.

9. The image management server according to claim 8, wherein the hardware processor selects a frame image to be transmitted to the external display apparatus from among a plurality of frame images forming the dynamic image or the dynamic analysis image attached to the radiology report, and acquires the selected frame image from the storage and transmits the acquired frame image to the external display apparatus.

10. A non-transitory recording medium storing a computer readable program causing a computer, disposed at a first location, of a display apparatus that includes a display to function as:

an acquirer that acquires, from an external apparatus disposed at a second location located remotely from the first location, a radiology report to which one or more thumbnails based on at least a part of a dynamic image acquired by irradiating and dynamically radiographing a subject with radiation at the second location or a dynamic analysis image indicating a result of analyzing the dynamic image is attached; and a display controller that causes the display to display the radiology report acquired by the acquirer;

wherein the display selects one thumbnail from the one or more thumbnails, and transmits an acquisition request for the dynamic image or the dynamic analysis image serving as a source of the selected thumbnail to the external device, and acquires the dynamic image or the dynamic analysis image serving as a source of the selected thumbnail from the external device that has responded to the acquisition request, wherein the display displays the dynamic image or the dynamic analysis image corresponding to the one image acquired.

11. A non-transitory recording medium storing a computer readable program causing a computer, disposed at a first location, to function as:

an acquirer that acquires a radiology report from storage disposed at a second location located remotely from the first location, that stores the radiology report, a dynamic image acquired by irradiating and dynamically radiographing a subject with radiation at the second location or a dynamic analysis image indicating a result of analyzing the dynamic image being attached to the radiology report; and an image generator that generates a display image for displaying the radiology report acquired by the acquirer on an external display apparatus;

wherein the computer selects one thumbnail from the one or more thumbnails, and transmits an acquisition request for the dynamic image or the dynamic analysis image serving as a source of the selected thumbnail to the external device, and acquires the dynamic image or the dynamic analysis image serving as a source of the selected thumbnail from the external device that has responded to the acquisition request, wherein the display displays the dynamic image or the dynamic analysis image corresponding to the one image acquired.

* * * * *